United States Patent
Suzuki et al.

(10) Patent No.: US 9,600,719 B2
(45) Date of Patent: Mar. 21, 2017

(54) CONTROL APPARATUS AND METHOD FOR EXERCISE THERAPY DEVICE

(71) Applicant: Mitsubishi Electric Engineering Company, Limited, Tokyo (JP)

(72) Inventors: Hironori Suzuki, Tokyo (JP); Yuichi Kimura, Tokyo (JP)

(73) Assignee: Mitsubishi Electric Engineering Company, Limited (JP)

(*) Notice: Subject to any disclaimer, the term of this patent is extended or adjusted under 35 U.S.C. 154(b) by 258 days.

(21) Appl. No.: 14/473,312

(22) Filed: Aug. 29, 2014

(65) Prior Publication Data

US 2015/0269426 A1  Sep. 24, 2015

(30) Foreign Application Priority Data

Mar. 19, 2014 (JP) .................................. 2014-056414

(51) Int. Cl.
*G07F 17/32* (2006.01)
*G06K 9/00* (2006.01)
*A61B 5/22* (2006.01)

(52) U.S. Cl.
CPC .......... *G06K 9/00496* (2013.01); *A61B 5/222* (2013.01)

(58) Field of Classification Search
USPC .................................. 700/90–93; 482/8, 54
See application file for complete search history.

(56) References Cited

U.S. PATENT DOCUMENTS

| | | | | |
|---|---|---|---|---|
| 4,244,021 A * | 1/1981 | Chiles, III | ............. | A61B 5/222 340/815.73 |
| 2007/0142179 A1* | 6/2007 | Terao | ................. | A63B 21/0056 482/8 |
| 2012/0253489 A1* | 10/2012 | Dugan | .................... | A63F 13/10 700/91 |
| 2013/0210580 A1* | 8/2013 | Watterson | ........... | G06F 19/3481 482/8 |
| 2014/0074265 A1* | 3/2014 | Arginsky | ........... | A63B 71/0622 700/91 |
| 2015/0051721 A1* | 2/2015 | Cheng | .................. | G06K 9/0055 700/91 |
| 2015/0141200 A1* | 5/2015 | Murray | ................ | A63B 21/154 482/5 |

* cited by examiner

*Primary Examiner* — Ronald Laneau
(74) *Attorney, Agent, or Firm* — Price Heneveld LLP

(57) ABSTRACT

Provided are a control apparatus and method for an exercise therapy device, including the following steps: calculating a first-order lag waveform of a waveform of the target value of the exercise physiological response as a corrected target value of the exercise physiological response using a response time constant; calculating a difference between the corrected target value of the exercise physiological response and the measured value of the exercise physiological response as an exercise physiological response deviation after correction; generating a command value for the exercise load based on the exercise physiological response deviation after correction, so that the exercise physiological response of the exerciser approaches the corrected target value of the exercise physiological response, to thereby control the exercise load to be applied to the exerciser.

7 Claims, 10 Drawing Sheets

CONTROL APPARATUS AND METHOD FOR EXERCISE THERAPY DEVICE

BACKGROUND OF THE INVENTION

1. Field of the Invention

The present invention relates to an exercise therapy device such as an ergometer and a treadmill, and more particularly, to a control apparatus and method for an exercise therapy device for controlling an exercise load to be applied to an exerciser so that a measured value of the exerciser's physiological response to exercise, such as his/her heart rate and pulse rate, approaches a preset target value.

2. Description of the Related Art

In a related-art exercise therapy device typified by a cycle ergometer, a rotation speed of pedals is measured with use of an encoder mounted to the device and further, a load torque applied to the pedals is measured based on a current value flowing through a load motor. The load motor is then controlled so that the thus acquired measured value of the rotation speed or load torque of the pedals approaches a target value of the rotation speed or load torque of the pedals (see, for example, Japanese Patent Application Laid-open No. Hei 10-179660).

There is also known an exercise therapy device for controlling the exercise load in accordance with a heart rate or a pulse rate, which is the exerciser's physiological response to exercise (hereinafter referred to as "exercise physiological response"). In such exercise therapy device, the rotation speed and load torque of the pedals are controlled so that a measured value of the exerciser's exercise physiological response reaches a target value of the exercise physiological response, which is preset in the exercise therapy device, to thereby adjust an exercise load to be applied to the exerciser (see, for example, Japanese Patent Application Laid-open No. Sho 63-35254).

In addition to the cycle ergometer, there is further known an exercise therapy device using, for example, a treadmill as such exercise therapy device for controlling the exercise load to be applied to the exerciser in accordance with the exerciser's exercise physiological response (see, for example, Japanese Patent Application Laid-open No. 2002-177413).

However, the related arts have the following problem.

In the exercise therapy device such as an ergometer and a treadmill, a delayed response time passing until the exerciser's heart rate follows a change of the exercise load to reach a state after the change differs depending on, for example, states of the exerciser's sympathetic nerves and parasympathetic nerves and the exerciser's response time constant including a dead time and a first-order lag as the exercise physiological response. In particular, the response time constant of the exercise physiological response of a patient with cardiac disease is known to become larger than that of a healthy person as the level of severity of the patient's heart failure becomes larger. For example, New York Heart Association (NYHA) classifies the level of severity of the heart failure as the NYHA classes, and a patient having the NYHA class associated with a higher level of severity has a larger response time constant of the heart rate.

However, in the related-art exercise therapy devices, such response time constant of the exerciser's heart rate has not been taken into consideration. Therefore, in a case of the exerciser who has a large response time constant such as a patient with cardiac disease, a deviation between the target value of the heart rate and the measured value thereof is undesirably larger than that of a healthy person. As a result, an amount of the exercise load increased by control of the exercise load becomes larger, and hence the exercise load is undesirably liable to exceed an upper limit value of the exercise load allowable for the exerciser or the exercise therapy device, which has been a problem of the related-art exercise therapy devices.

SUMMARY OF THE INVENTION

The present invention has been made in order to solve the above-mentioned problem, and has an object to provide a control apparatus and method for an exercise therapy device capable of more appropriately controlling an exercise load so as not to apply an excessive load to an exerciser even when a response time constant of the exerciser's exercise physiological response, such as his/her heart rate and pulse rate, differs from one exerciser to another.

According to one embodiment of the present invention, there is provided a control apparatus for an exercise therapy device, the exercise therapy device including an arithmetic control part for controlling an exercise load to be applied to an exerciser so that a measured value of one of a heart rate and a pulse rate of the exerciser, which are each an exercise physiological response of the exerciser, approaches a preset target value of the exercise physiological response. The arithmetic control part is configured to: set the preset target value of the exercise physiological response and a response time constant of the exercise physiological response of the exerciser in a storage part of the exercise therapy device in response to an input operation of the exerciser; use the response time constant to calculate a first-order lag waveform of a waveform of the preset target value of the exercise physiological response as a corrected target value of the exercise physiological response; calculate a difference between the preset target value of the exercise physiological response and the measured value of the exercise physiological response as an exercise physiological response deviation before correction; calculate a difference between the corrected target value of the exercise physiological response and the measured value of the exercise physiological response as an exercise physiological response deviation after correction; and generate, based on the exercise physiological response deviation before correction and the exercise physiological response deviation after correction, a command value for the exercise load so that the exercise physiological response of the exerciser approaches one of the preset target value of the exercise physiological response and the corrected target value of the exercise physiological response, to thereby control the exercise load to be applied to the exerciser.

Further, according to one embodiment of the present invention, there is provided a control method for an exercise therapy device, the exercise therapy device including an arithmetic control part for controlling an exercise load to be applied to an exerciser so that a measured value of one of a heart rate and a pulse rate of the exerciser, which are each an exercise physiological response of the exerciser, approaches a preset target value of the exercise physiological response. The control method includes: setting, by the arithmetic control part, the preset target value of the exercise physiological response and a response time constant of the exercise physiological response of the exerciser in a storage part of the exercise therapy device in response to an input operation of the exerciser; using, by the arithmetic control part, the response time constant to calculate a first-order lag waveform of a waveform of the preset target value of the exercise physiological response as a corrected target value of the exercise physiological response; calculating, by the arithmetic control part, a difference between the preset target value of the exercise physiological response and the measured value of the exercise physiological response as an exercise physiological response deviation before correction; calculating, by the arithmetic control part, a difference between the corrected target value of the exercise physiological response and the measured value of the exercise physiological response as an exercise physiological response deviation after correction; and generating, by the arithmetic control part, based on the exercise physiological response deviation before correction and the exercise physiological response deviation after correction, a command value for the exercise load so that the exercise physiological response of the exerciser approaches one of the preset target value of the exercise physiological response and the corrected target value of the exercise physiological response, to thereby control the exercise load to be applied to the exerciser.

According to one embodiment of the present invention, in the exercise therapy device for controlling the exercise load to be applied to the exerciser so that the measured value of the exerciser's exercise physiological response, such as his/her heart rate and pulse rate, approaches the preset target value, the exercise load to be applied to the exerciser is controlled in accordance with the response time constant of the exercise physiological response of each exerciser based on the information related to the response time constant input and set by the exerciser. As a result, it is possible to provide the control apparatus and method for an exercise therapy device capable of appropriately controlling the exercise load so as not to apply an excessive load to the exerciser even when the response time constant of the exerciser's exercise physiological response differs from one exerciser to another.

DETAILED DESCRIPTION OF THE PREFERRED EMBODIMENTS

Figure 1:
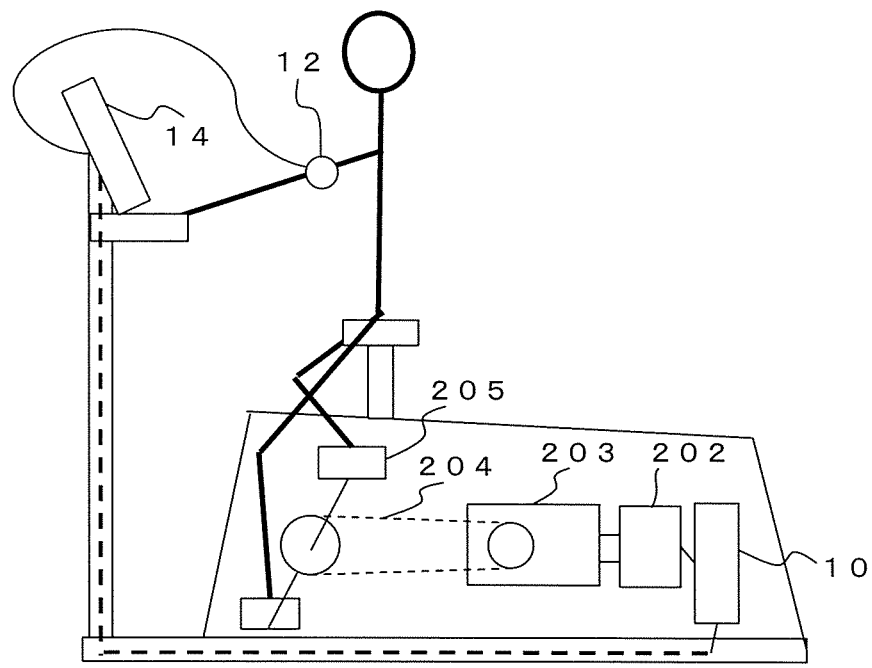
FIG. 1 is a diagram illustrating an example of a configuration adopted in a case where a cycle ergometer is used as an exercise therapy device according to a first embodiment of the present invention.

A description is now given of a control apparatus and method for an exercise therapy device according to an exemplary embodiment of the present invention with reference to the accompanying drawings. Note that, throughout the drawings, like or corresponding components are denoted by like reference numerals to describe those components. Further, in the following, a description is first given of an overview of the related art with reference to FIGS. 13 and 14, and after that, a detailed description is given of a configuration and effects of the present invention with reference to FIGS. 1 to 12.

First Embodiment

There has already been known an exercise therapy device for controlling an exercise load to be applied to an exerciser so that a measured value of the exerciser's exercise physiological response, such as his/her heart rate and pulse rate (in the following description, the "heart rate", which is one of the exercise physiological responses, is adopted), approaches a preset target value.

A related-art exercise therapy device is configured to, as a method of causing the exerciser's heart rate to approach the target value, compare the target value of the exerciser's heart rate (hereinafter referred to as "target heart rate value") with a measured value of the exerciser's current heart rate (hereinafter referred to as "measured heart rate value"). When it is then determined that the measured heart rate value is smaller than the target heart rate value, the exercise therapy device increases the exercise load to be applied to the exerciser in order to increase the exerciser's heart rate. On the other hand, when it is determined that the measured heart rate value is larger than the target heart rate value, the exercise therapy device decreases the exercise load to be applied to the exerciser in order to decrease the exerciser's heart rate.

Figure 13:
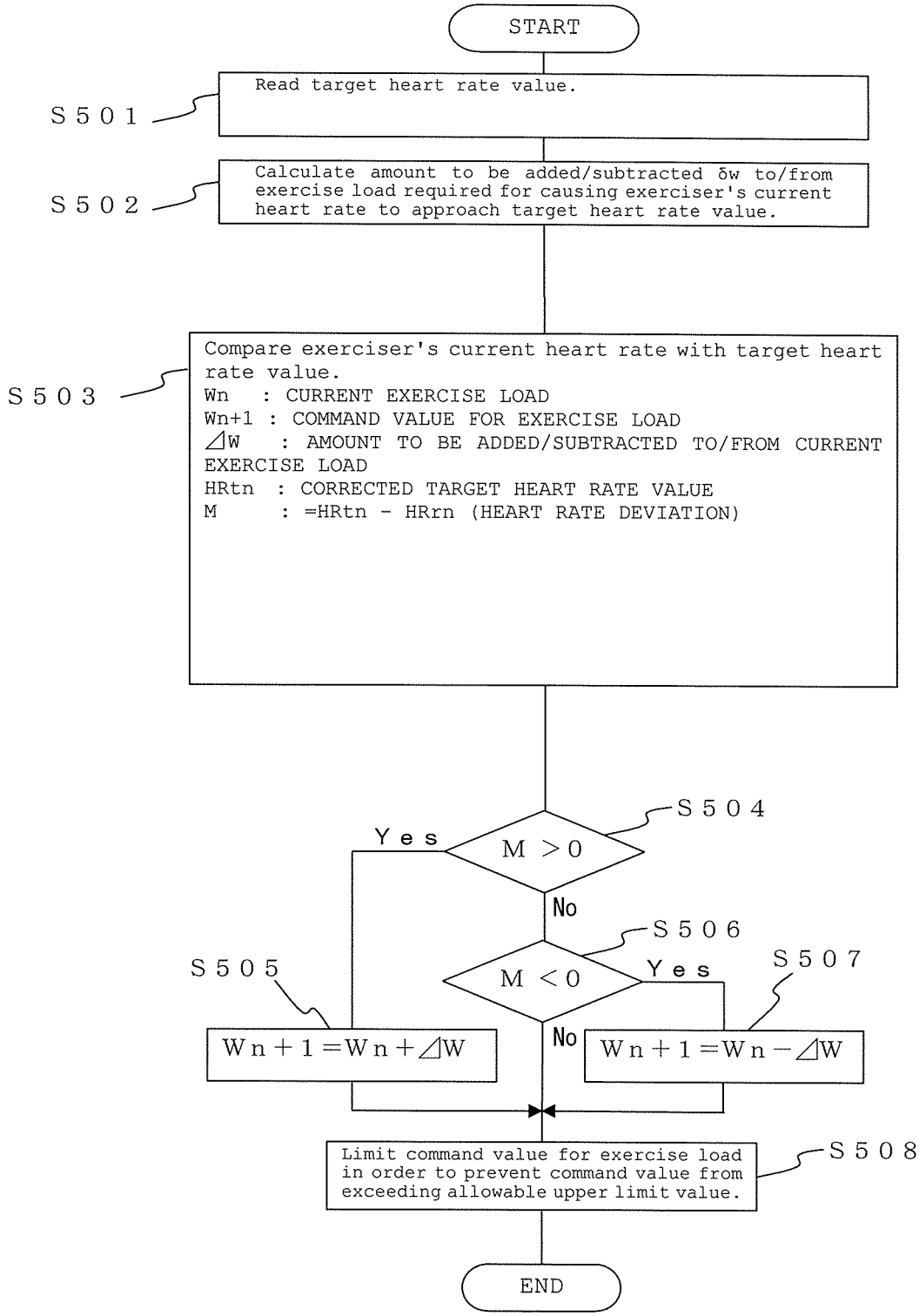
FIG. 13 is a flow chart illustrating a method of controlling a related-art exercise therapy device.

FIG. 13 is a flow chart illustrating a method of controlling the related-art exercise therapy device. First, referring to FIG. 13, a description is given of a method of controlling an exercise load to be performed by the related-art exercise therapy device.

First, in Step S501, the exercise therapy device reads the target heart rate value preset in a control apparatus. Then, in Step S502, the exercise therapy device calculates a heart rate deviation, which is a difference between the target heart rate value and the measured heart rate value, and based on the heart rate deviation, calculates an amount to be added/subtracted $\Delta W$ to/from the exercise load required for causing the exerciser's heart rate to approach the target heart rate value.

Next, in Step S503, the exercise therapy device compares the measured heart rate value with the target heart rate value. As a result of the comparison, in Step S504, when the target heart rate value is larger than the measured heart rate value, the processing proceeds to Step S505, and the exercise therapy device adds the amount to be added/subtracted $\Delta W$ to/from the exercise load appropriate for the heart rate deviation to the current exercise load, to thereby set the obtained value as a command value for the exercise load.

Next, in Step S506, when the target heart rate value is smaller than the measured heart rate value, the processing proceeds to Step S507, and the exercise therapy device subtracts the amount to be added/subtracted $\Delta W$ to/from the exercise load appropriate for the heart rate deviation from the current exercise load, to thereby set the obtained value as the command value for the exercise load.

Finally, in Step S508, in order to prevent the command value for the exercise load from exceeding an upper limit value allowable for the exerciser or the exercise therapy device, the exercise therapy device clamps the command value for the exercise load. To be specific, for example, when the command value for the exercise load exceeds a preset upper limit value, the exercise therapy device sets this upper limit value as the command value for the exercise load.

However, in the above-mentioned related-art exercise therapy device, as described above, a response time constant of the exerciser's heart rate is not taken into consideration. Therefore, in a case of an exerciser whose response time constant is large such as a patient with cardiac disease, an integrated value of the amount to be added/subtracted to/from the exercise load in a transitional period during which the heart rate is changing becomes undesirably large. As a result, the command value for the exercise load is undesirably liable to exceed an upper limit value of the exercise load allowable for the exerciser or the exercise therapy device, which has been a problem of the related-art exercise therapy device.

Figure 14:
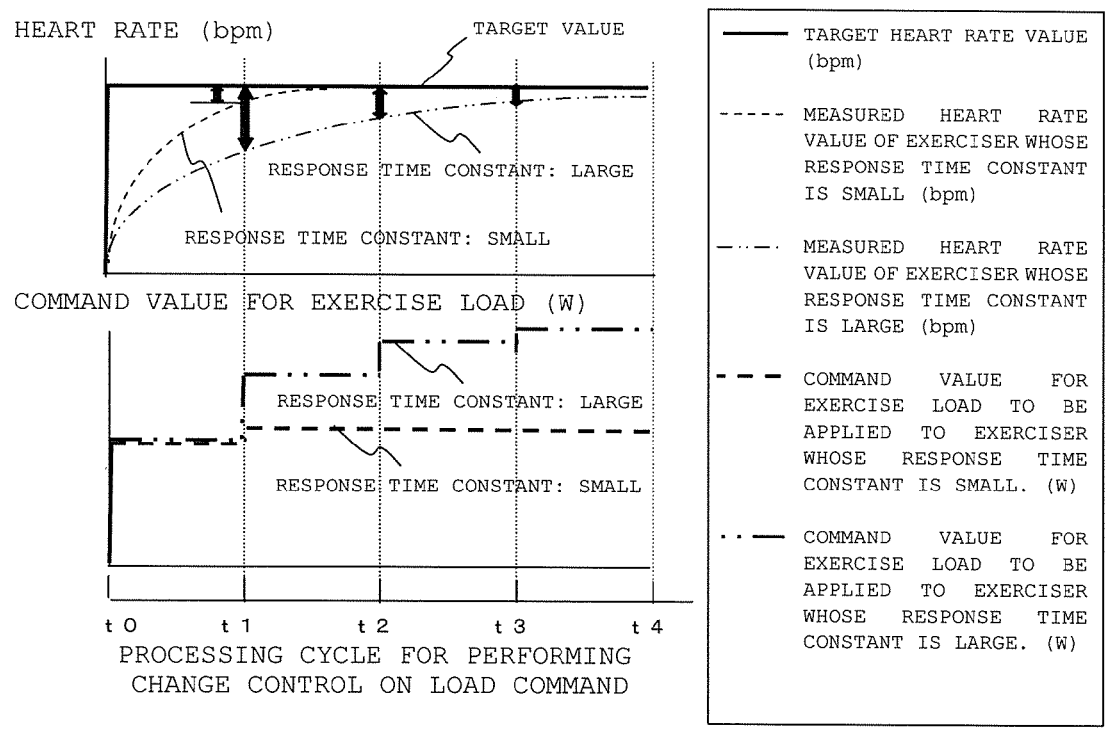
FIG. 14 is a graph showing a command value for an exercise load obtained in a case where a response time constant of the exerciser's heart rate is not taken into consideration in the related-art exercise therapy device.

FIG. 14 is a graph showing the command value for the exercise load obtained in a case where the response time constant of the exerciser's heart rate is not taken into consideration in the related-art exercise therapy device. With the method of controlling the related-art exercise therapy device, as shown in FIG. 14, even after the response time constant of the heart rate passes and the heart rate becomes stable at a changed value, the command value for the exercise load undesirably far exceeds the target value of the exercise load owing to an excessive increase of the exercise load during a transitional state of the heart rate.

Moreover, a fluctuation of the command value for the exercise load may occur in the following manner. Specifically, when such excessive command value for the exercise load is reflected in the current exercise load, the exerciser's heart rate increases in contrast and far exceeds the target heart rate value, and in turn, the command value for the exercise load steeply decreases and becomes insufficient. As a result, not only prescribed control for the exercise load is not performed appropriately, but also an excessive exercise load is undesirably applied to the exerciser, which has also been a problem of the related-art exercise therapy device.

In view of the above-mentioned problems, referring to FIGS. 1 to 6, a description is given of a control apparatus for an exercise therapy device according to a first embodiment of the present invention in which the exerciser's heart rate is taken into consideration. FIG. 1 is a diagram illustrating an example of a configuration adopted in a case where a cycle ergometer is used as the exercise therapy device according to the first embodiment of the present invention.

The exercise therapy device according to the first embodiment of the present invention illustrated in FIG. 1 includes a load motor control device 10, a heart rate detection sensor 12, a control apparatus 14, a load motor 202, a speed reducer 203, a transfer mechanism 204, and pedals 205.

The heart rate detection sensor 12 is attached to the exerciser, measures the exerciser's heart rate, and outputs the measured heart rate to the control apparatus 14. The control apparatus 14 takes in the measured heart rate value output from the heart rate detection sensor 12, calculates such a command value for the exercise load as to cause the measured heart rate value to approach the target heart rate value, and outputs the calculated command value to the load motor control device 10.

The load motor control device 10 causes a current corresponding to the command value for the exercise load output from the control apparatus 14 to flow through the load motor 202. The load motor 202 outputs a rotation torque corresponding to the current value output from the load motor control device 10, and generates the exercise load on the pedals 205 via the speed reducer 203 and the transfer mechanism 204.

Figure 2:
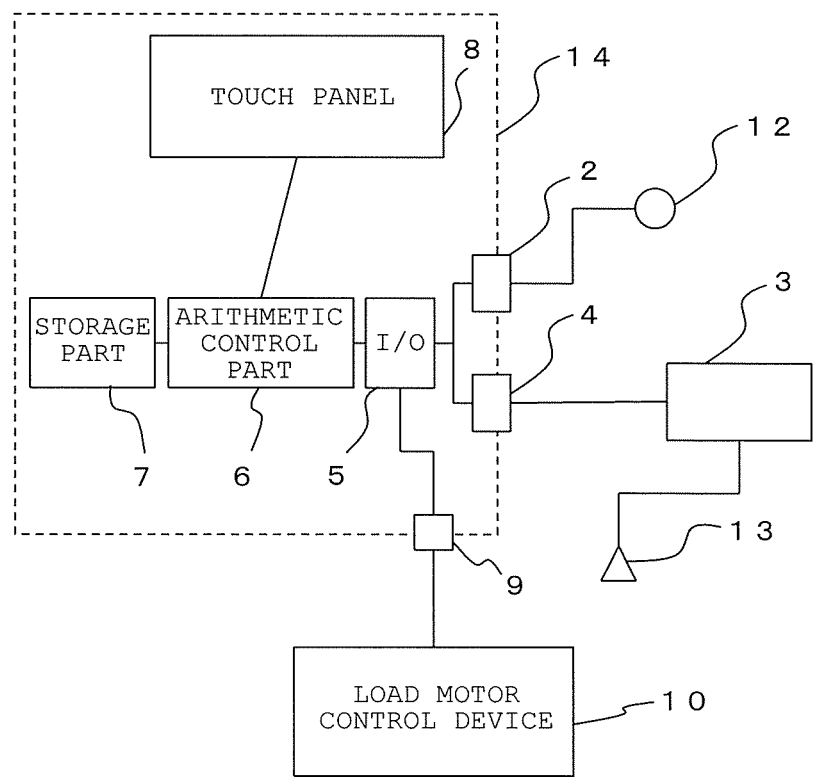
FIG. 2 is a diagram illustrating an example of an internal configuration of a control apparatus for an exercise therapy device according to the first embodiment of the present invention.

FIG. 2 is a diagram illustrating an example of an internal configuration of the control apparatus 14 for the exercise therapy device according to the first embodiment of the present invention. The exerciser uses the control apparatus 14 to make input settings for the exercise therapy device and check the state of the exercise therapy device. The control apparatus 14 includes a touch panel 8, an arithmetic control part 6, a storage part 7, an I/O 5, a sensor input interface 2, an external device communication interface 4, and a load motor control device interface 9.

The control apparatus 14 inputs the measured heart rate value output from the heart rate detection sensor 12 via the sensor input interface 2. Note that, in this case, the control apparatus 14 may also input via the external device communication interface 4, as the measured heart rate value, communication data output from an external heart rate detection sensor 13 via a load control device communication interface 3. The measured heart rate value that has been input to the control apparatus 14 is input to the arithmetic control part 6 via the I/O 5.

Figure 3:
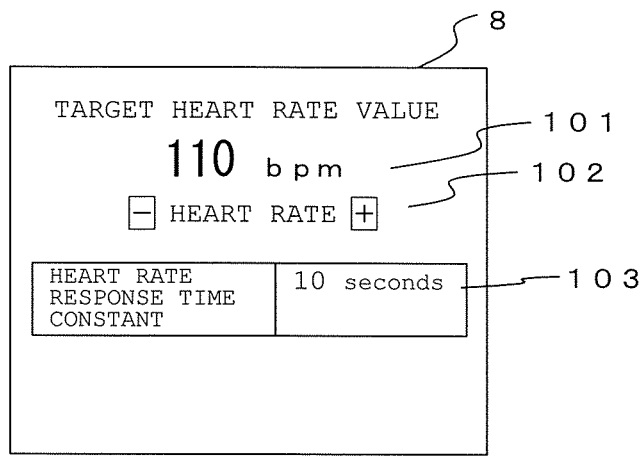
FIG. 3 is a diagram illustrating an example of a user interface displayed on a touch panel of the exercise therapy device according to the first embodiment of the present invention.

FIG. 3 is a diagram illustrating an example of a user interface displayed on the touch panel 8 of the exercise therapy device according to the first embodiment of the present invention. When the exerciser's target heart rate value and response time constant of the heart rate are input to a target heart rate display setting part 101 and a response time constant setting display part 103 of the touch panel 8, respectively, the arithmetic control part 6 sets the input target heart rate value and response time constant in the storage part 7. Note that, in this case, the exerciser's target heart rate value may be specified by increasing/decreasing the value with "+" or "−" displayed in a target heart rate increase/decrease setting display part 102.

Next, the arithmetic control part 6 uses the response time constant to correct the target heart rate value as described later, and calculates such a command value for the exercise load as to cause the exerciser's heart rate to approach the corrected target heart rate value and outputs the calculated command value to the load motor control device 10 via the load motor control device interface 9.

Note that, in FIG. 3, the touch panel 8 is used as a device for inputting the target heart rate value and the response time constant, but the input device is not limited to the touch panel 8. Any type of input device may be used as long as the input device to be used has such a minimum function as to enable inputting of information, such as the response time constant of the exercise physiological response. For example, it is also possible to use, instead of the touch panel 8, a speech recognition device for inputting the information, such as the response time constant of the exercise physiological response, by giving a voice command.

Figure 4:
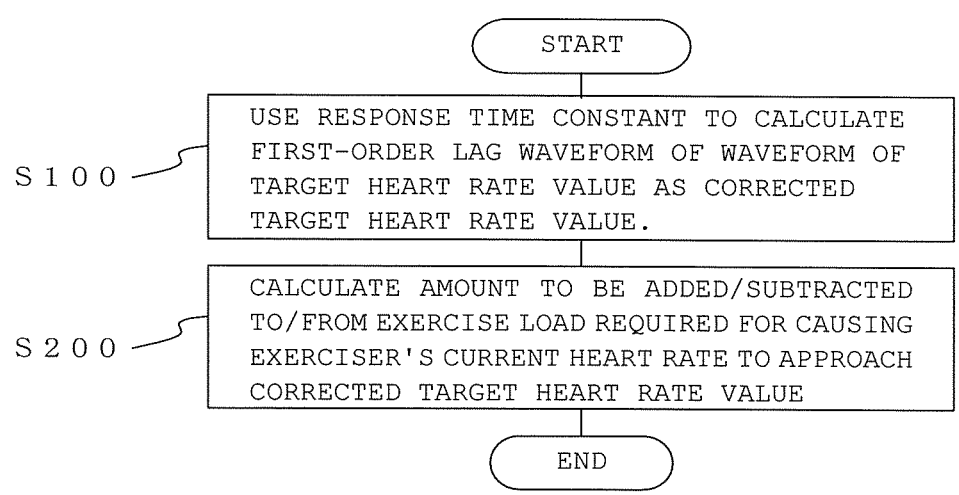
FIG. 4 is a flow chart illustrating an overview of a method of controlling an exercise therapy device according to the first embodiment of the present invention.

FIG. 4 is a flow chart illustrating an overview of a method of controlling an exercise therapy device according to the first embodiment of the present invention. FIG. 4 illustrates an overview of heart rate control of controlling the exercise load to be applied to the exerciser so that the exerciser's measured heart rate value approaches the target heart rate value.

In the flow chart illustrated in FIG. 4, in Step S100, the arithmetic control part 6 uses the response time constant to calculate a first-order lag waveform of the waveform of the target heart rate value as the corrected target heart rate value. Specifically, the arithmetic control part 6 corrects the target heart rate value so that the corrected target heart rate value has such a waveform that the target heart rate value before the change changes exponentially with the response time constant toward the target heart rate value after the change.

Next, in Step S200, the arithmetic control part 6 subtracts the measured heart rate value from the corrected target heart rate value to calculate the heart rate deviation, and based on the heart rate deviation, calculates the amount to be added/subtracted $\Delta W$ to/from the exercise load required for causing the exerciser's heart rate to approach the corrected target heart rate value. To be specific, for example, the arithmetic control part 6 sets, as the amount to be added/subtracted $\Delta W$ to/from the exercise load, a value obtained by multiplying the heart rate deviation by a preset gain.

Figure 5:
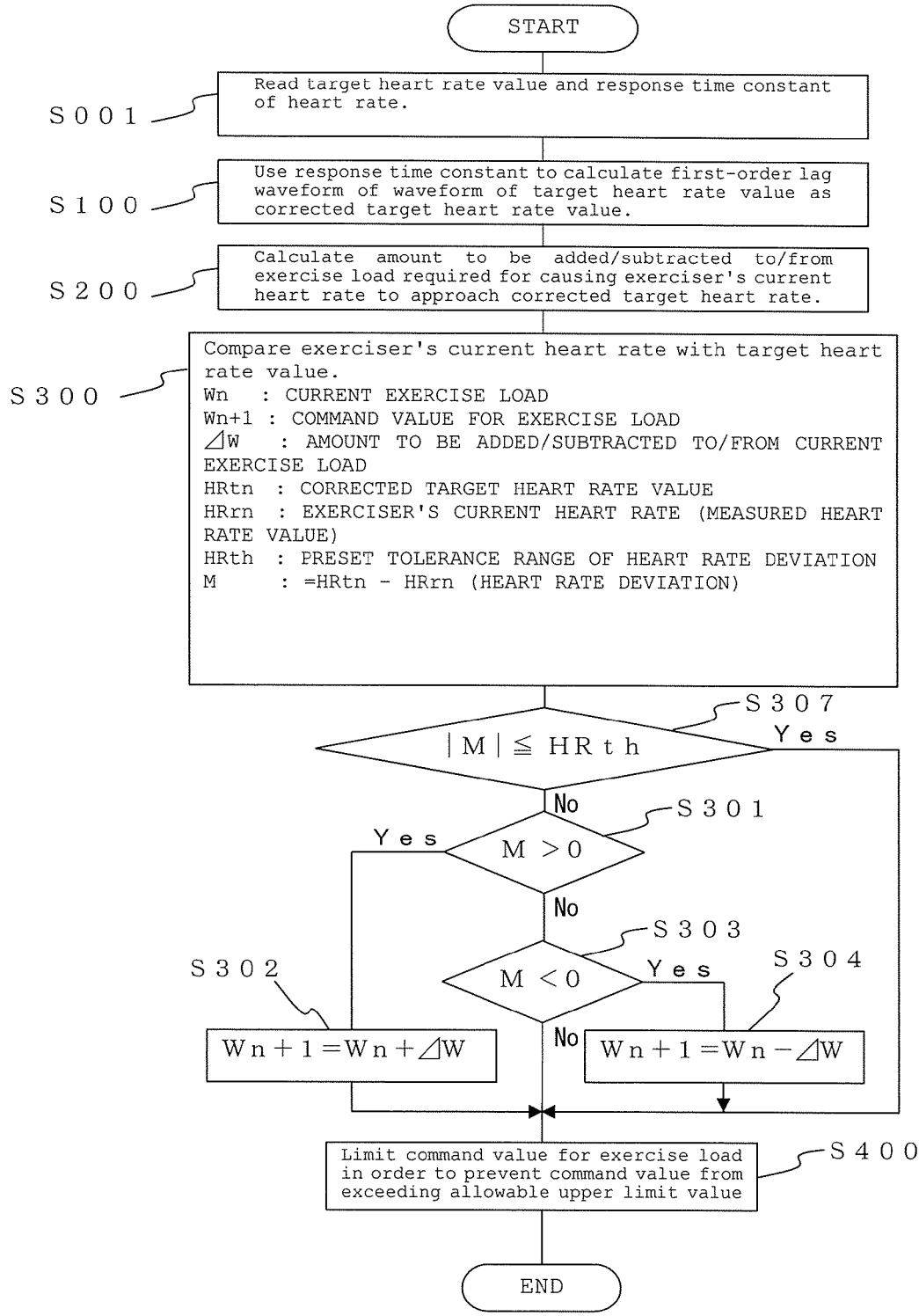
FIG. 5 is a flow chart illustrating details of the method of controlling an exercise therapy device according to the first embodiment of the present invention.

FIG. 5 is a flow chart illustrating details of the method of controlling an exercise therapy device according to the first embodiment of the present invention. Now, referring to FIG. 5, a description is given of the heart rate control illustrated in FIG. 4 in more detail.

In Step S001, the arithmetic control part 6 first reads the target heart rate value and the response time constant, which are set in the storage part 7. The arithmetic control part 6 then performs the same processing as that of Steps S100 and S200 illustrated in FIG. 4.

Next, in Step S300, the arithmetic control part 6 compares the corrected target heart rate value with the measured heart rate value. As a result of the comparison, in Step S307, when an absolute value M of the heart rate deviation falls within a tolerance range HRth of the heart rate deviation preset in the storage part 7, the arithmetic control part 6 sets a current exercise load Wn as a command value for exercise load Wn+1 as it is.

Next, in Step S301, when the heart rate deviation is positive, in other words, when the corrected target heart rate value is larger than the measured heart rate value, the arithmetic control part 6 determines that the exercise load is insufficient. Then, in Step S302, the arithmetic control part 6 sets Wn+$\Delta W$, which is obtained by adding the amount to be added/subtracted $\Delta W>0$ to/from the exercise load to the current exercise load Wn, as the command value for exercise load Wn+1.

Next, in Step S303, when the heart rate deviation is negative, in other words, when the corrected target heart rate value is smaller than the measured heart rate value, the arithmetic control part 6 determines that the exercise load is excessive. Then, in Step S304, the arithmetic control part 6 sets Wn−$\Delta W$, which is obtained by subtracting the amount to be added/subtracted $\Delta W>0$ to/from the exercise load from the current exercise load Wn, as the command value for exercise load Wn+1.

Next, in Step S400, in order to prevent the command value for the exercise load from exceeding an upper limit value allowable for the exerciser or the exercise therapy device, the arithmetic control part 6 clamps the command value for the exercise load. To be specific, for example, when the command value for the exercise load exceeds a preset upper limit value, the arithmetic control part 6 sets this upper limit value as the command value for the exercise load.

Figure 6:
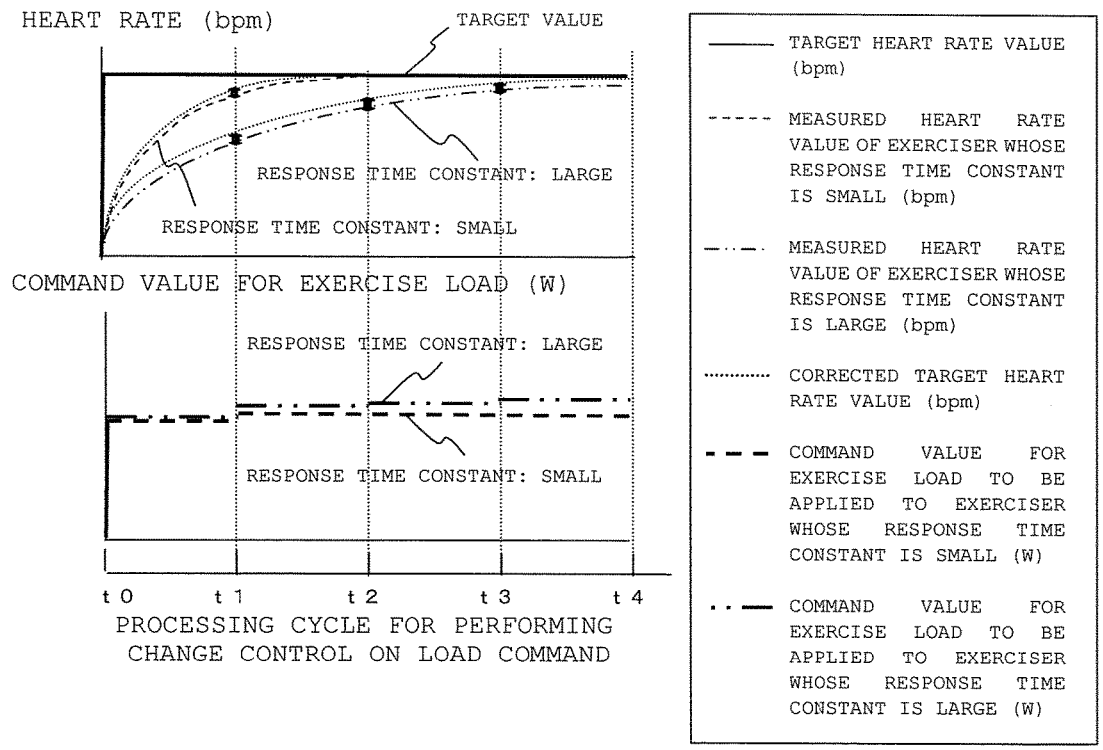
FIG. 6 is a graph showing a command value for an exercise load obtained in a case where a response time constant of the exerciser's heart rate is taken into consideration in the exercise therapy device according to the first embodiment of the present invention.

FIG. 6 is a graph showing the command value for the exercise load obtained in a case where the response time constant of the exerciser's heart rate is taken into consideration in the exercise therapy device according to the first embodiment of the present invention. In FIG. 6, even in a case where a delayed response time observed when the exerciser's heart rate changes while following a change of the exercise load is large, the set response time constant is used to calculate the first-order lag waveform of the waveform of the target heart rate value as the corrected target heart rate value. As a result, the heart rate deviation, which is the difference between the corrected target heart rate value and the measured heart rate value, is minute, and hence the command value for the exercise load calculated based on the heart rate deviation increases little.

Further, when the heart rate deviation falls within the preset tolerance range of the heart rate deviation, the command value for the exercise load is stable without a change. As a result, even when the response time constant of the heart rate is large, after a sufficient period of time appropriate for such a large response time passes, the exerciser's heart rate reaches the target heart rate value. In other words, irrespective of whether the response time constant is large or small, the measured heart rate value follows the target heart rate value having the first-order lag waveform without much deviation.

As described above, in the first embodiment, the exercise load to be applied to the exerciser is controlled in accordance with the response time constant of the exercise physiological response of each exerciser. As a result, even when the response time constant of the exerciser's exercise physiological response differs from one exerciser to another, it is possible to appropriately control the exercise load so as not to apply an excessive load to the exerciser. Moreover, the exerciser can effectively carry out an exercise therapy as prescribed in an exercise prescription.

Further, the response time constant is used to calculate the first-order lag waveform of the waveform of the target heart rate value as the corrected target heart rate value. It is therefore possible to estimate an actual waveform during a transitional state of the exerciser's heart rate with a high accuracy to appropriately control the exercise load.

Note that, in Step S200 of FIG. 5, the amount to be added/subtracted $\Delta W$ to/from the exercise load is calculated based on the heart rate deviation between the corrected target heart rate value and the measured heart rate value, but may be calculated based on a deviation between the target heart rate value before correction and the measured heart rate value instead. Even in this case, in Step S307, the current exercise load Wn is set as it is as the command value for exercise load Wn+1 when the heart rate deviation between the corrected target heart rate value and the measured heart rate value falls within the tolerance range HRth of the heart rate deviation, and hence it is possible to control the exercise load so as not to apply an excessive exercise load to the exerciser.

Further, in the invention described above, it is assumed that the present invention is applied to the exercise therapy device such as an ergometer with which the exerciser operates the pedals to carry out training, but the present invention is not limited thereto. The present invention is also applicable to, for example, an exercise therapy device such as a treadmill.

Further, in the description given above, the heart rate is used as the exerciser's exercise physiological response, but it is possible to acquire similar effects even when the pulse rate is used instead of the heart rate.

Second Embodiment

In the first embodiment described above, a description has been given of the method of correcting the waveform of the target heart rate value as the first-order lag waveform that changes exponentially with the response time constant. In contrast, in a second embodiment of the present invention, a description is given of a method of correcting, after modifying the waveform of the target heart rate value that changes in a stepwise manner to a waveform that changes at a constant rate of change during a given period of time, the modified waveform as the first-order lag waveform.

Figure 7:
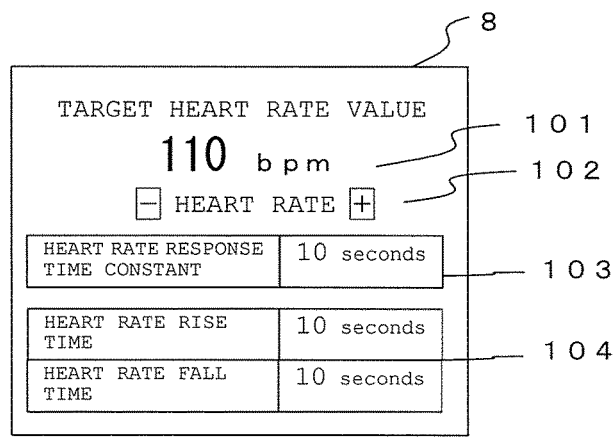
FIG. 7 is a diagram illustrating an example of a user interface displayed on a touch panel of the exercise therapy device according to a second embodiment of the present invention.

FIG. 7 is a diagram illustrating an example of a user interface displayed on the touch panel 8 of the exercise therapy device according to the second embodiment of the present invention. In the user interface of the second embodiment illustrated in FIG. 7, a given change period setting display part 104 is further added to the user interface of the first embodiment illustrated in FIG. 3.

When a heart rate rise time and a heart rate fall time are input to the given change period setting display part 104 of the touch panel 8, the arithmetic control part 6 sets the input heart rate rise time and heart rate fall time in the storage part 7.

Figure 8:
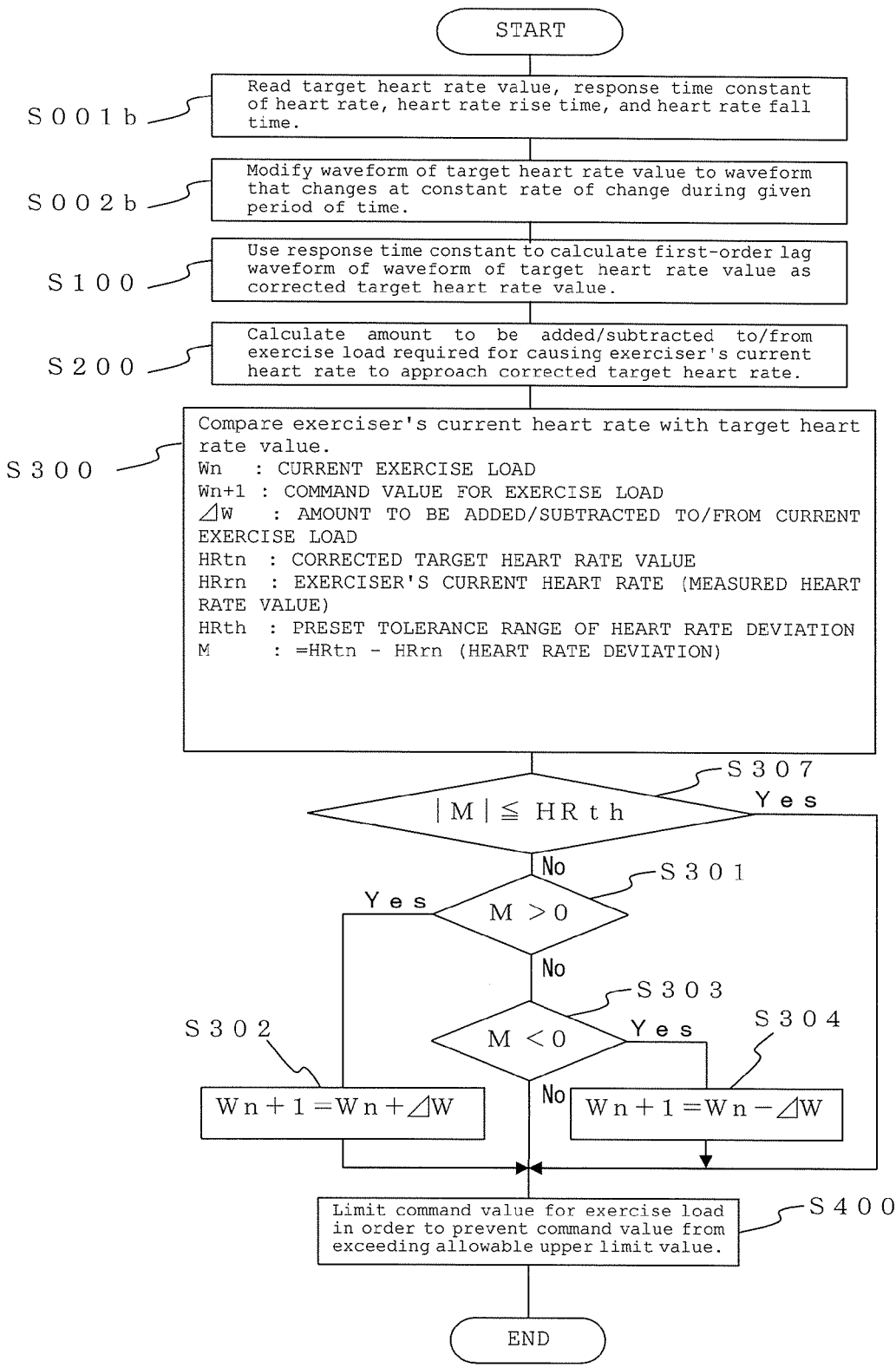
FIG. 8 is a flow chart illustrating a method of controlling an exercise therapy device according to the second embodiment of the present invention.
Figure 9:
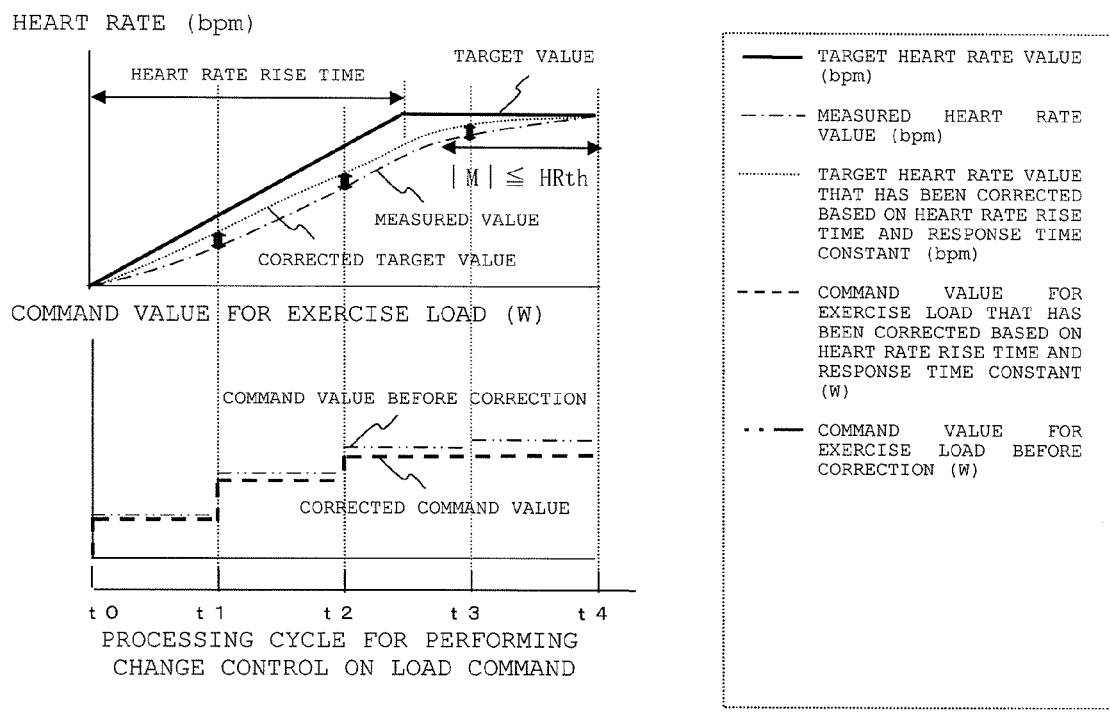
FIG. 9 is a graph showing a method of modifying a waveform of a target heart rate value to a waveform that changes at a constant rate of change during a given period of time in the exercise therapy device according to the second embodiment of the present invention.

FIG. 8 is a flow chart illustrating a method of controlling an exercise therapy device according to the second embodiment of the present invention. Further, FIG. 9 is a graph showing a method of modifying the waveform of the target heart rate value to a waveform that changes at a constant rate of change during a given period of time in the exercise therapy device according to the second embodiment of the present invention. In the flow chart of the second embodiment illustrated in FIG. 8, as compared with the flow chart of the first embodiment illustrated in FIG. 5, the processing of Step S001b differs from that of Step S001 and Step S002b is added. Other steps are the same as those of the first embodiment described above.

In the flow chart illustrated in FIG. 8, in Step S001b, the arithmetic control part 6 first reads the target heart rate value, the response time constant of the heart rate, the heart rate rise time, and the heart rate fall time, which are set in the storage part 7. Next, in Step S002b, the arithmetic control part 6 modifies the waveform of the target heart rate value that changes in a stepwise manner to the waveform that changes at a constant rate of change during a given period of time as shown in FIG. 9.

After that, the arithmetic control part 6 performs the same processing to be performed after Step S100 of FIG. 5 of the first embodiment described above on the target heart rate value whose waveform has been modified to the waveform that changes at the constant rate of change during the given period of time.

As described above, in the second embodiment, the waveform of the target heart rate value that changes in a stepwise manner is modified to the waveform that changes at the constant rate of change during the given period of time, and then the modified waveform is further corrected as the first-order lag waveform. As a result, it is possible to estimate an actual waveform during the transitional state of the exerciser's heart rate with a higher accuracy to appropriately control the exercise load.

Further, the exercise load to be applied to the exerciser increases gradually with an amount appropriate for the heart rate rise time and decreases gradually with an amount appropriate for the heart rate fall time, and hence it is possible to gradually alleviate the load to be applied to the exerciser due to the applied exercise load. For example, in FIG. 9, the load corresponding to the response time constant of the exerciser's heart rate does not rise steeply to the target value for the exercise load, and hence it is possible to alleviate the exercise load to be applied to the exerciser. Note that, in FIG. 9, a time width that is wider than an actual width is shown in order to make a processing time to easily visible, but actually, the processing time is far shorter than the heart rate rise time, and hence an increased amount of the exercise load also becomes gradually larger.

Third Embodiment

In a third embodiment of the present invention, a description is given of a method of setting the response time constant by specifying one of the NYHA classes, which are classification levels of severity of a heart failure.

Figure 10:
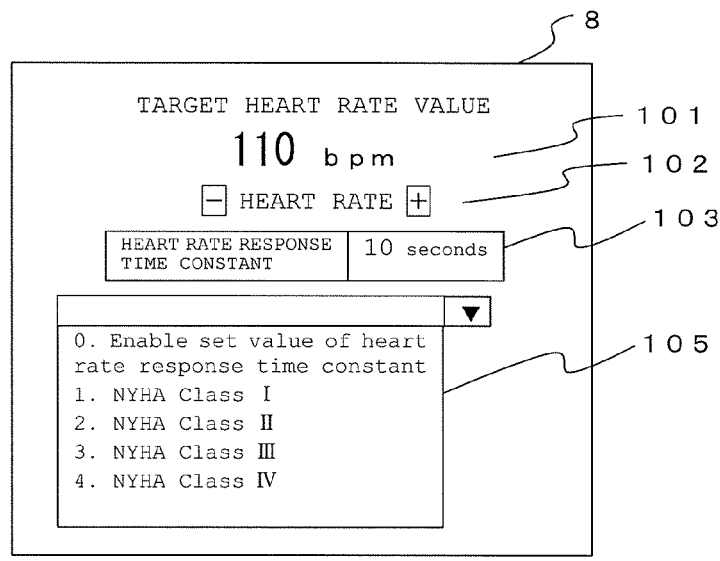
FIG. 10 is a diagram illustrating an example of a user interface displayed on a touch panel of the exercise therapy device according to a third embodiment of the present invention.

FIG. 10 is a diagram illustrating an example of a user interface displayed on the touch panel 8 of the exercise therapy device according to the third embodiment of the present invention. In the user interface of the third embodiment illustrated in FIG. 10, an NYHA class setting display part 105 is further added to the user interface of the first embodiment described above illustrated in FIG. 3. In the NYHA class setting display part 105, the NYHA class can be input or selected.

When one of the NYHA classes, which are the classification levels of severity of a heart failure defined by New York Heart Association (NYHA), is input to the NYHA class setting display part 105 of the touch panel 8, the arithmetic control part 6 sets the input NYHA class in the storage part 7.

In the storage part 7 of the third embodiment, a table defining a relationship between each of the NYHA classes and the response time constant of the heart rate is stored in advance. The arithmetic control part 6 can refer to this table to acquire a corresponding response time constant of the heart rate based on the NYHA class specified in the NYHA class setting display part 105.

To be specific, for example, in FIG. 10, when one of "1" to "4" is set in the NYHA class setting display part 105, the response time constant associated with corresponding one of NYHA Classes I to IV is read. When "0" is set in the NYHA class setting display part 105, the response time constant set in the response time constant setting display part 103 becomes enabled.

Figure 11:
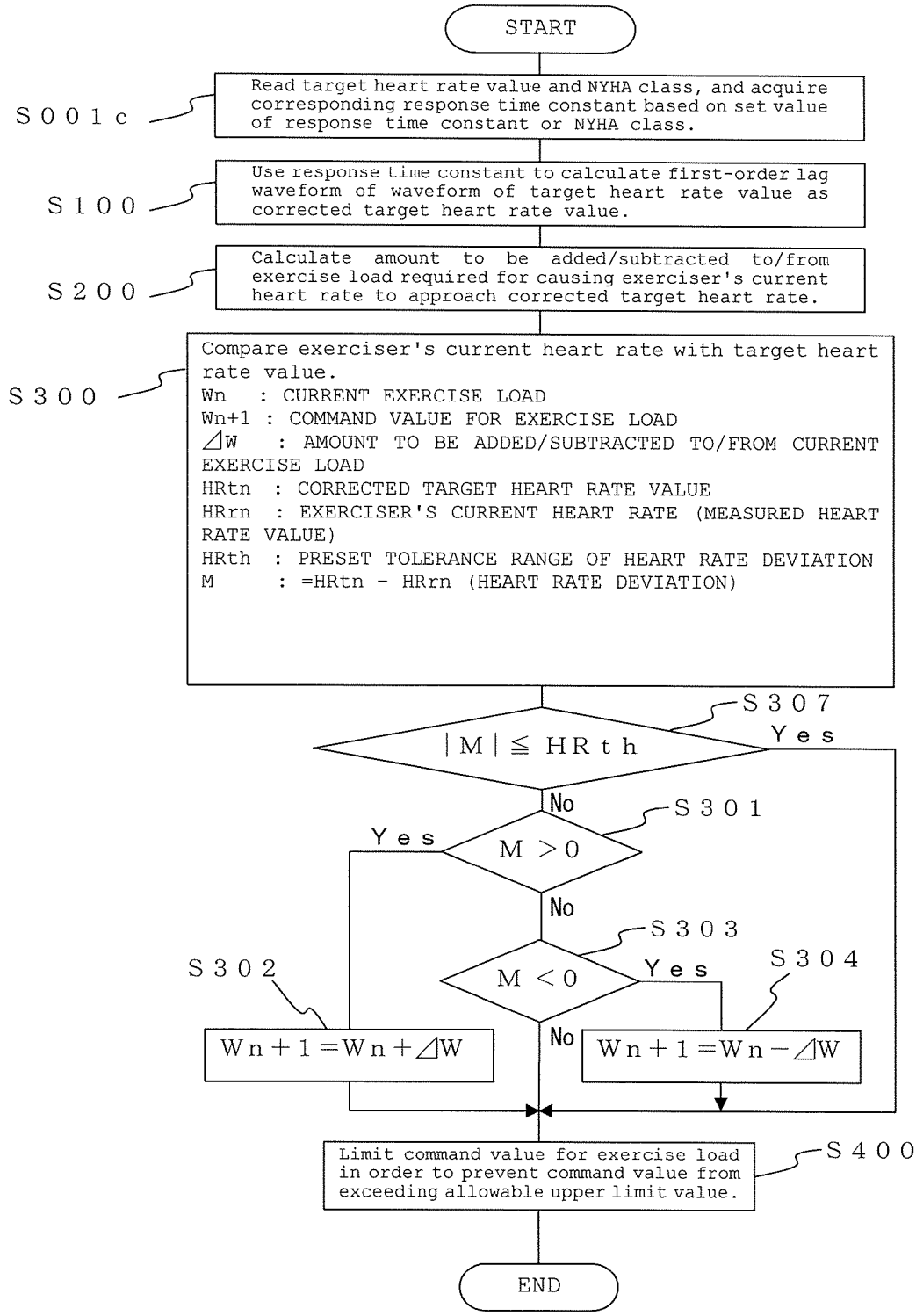
FIG. 11 is a flow chart illustrating a method of controlling an exercise therapy device according to a third embodiment of the present invention.

FIG. 11 is a flow chart illustrating a method of controlling an exercise therapy device according to the third embodiment of the present invention. In the flow chart of the third embodiment illustrated in FIG. 11, as compared with the flow chart of the first embodiment illustrated in FIG. 5, the processing of Step S001c differs from that of Step S001. Other steps are the same as those of the first embodiment described above.

In Step S001c, the arithmetic control part 6 reads the target heart rate value and the NYHA class, which are set in the storage part 7, and refers to the table defining the relationship between each of the NYHA classes and the response time constant of the heart rate, which is also stored in the storage part 7, to acquire the corresponding response time constant of the heart rate based on the NYHA class. Processing to be performed after Step S100 is the same as that of the first embodiment illustrated in FIG. 5.

As described above, in the third embodiment, in the user interface displayed on the touch panel 8, it is possible to select one of a total of five options, that is, setting the response time constant and setting one of the NYHA classes (four levels), as a set value of the response time constant of the heart rate to be set in the storage part 7. As a result, even without measuring the response time constant of the exerciser's heart rate in advance, it is possible to set the response time constant of the heart rate by specifying one of the NYHA classes instead.

Fourth Embodiment

In a fourth embodiment of the present invention, a description is given of a method of notifying of an abnormality of the exerciser's heart rate response when the delayed response time passing until the exerciser's heart rate follows a change of the exercise load to reach a state after the change exceeds a preset period of time.

Figure 12:
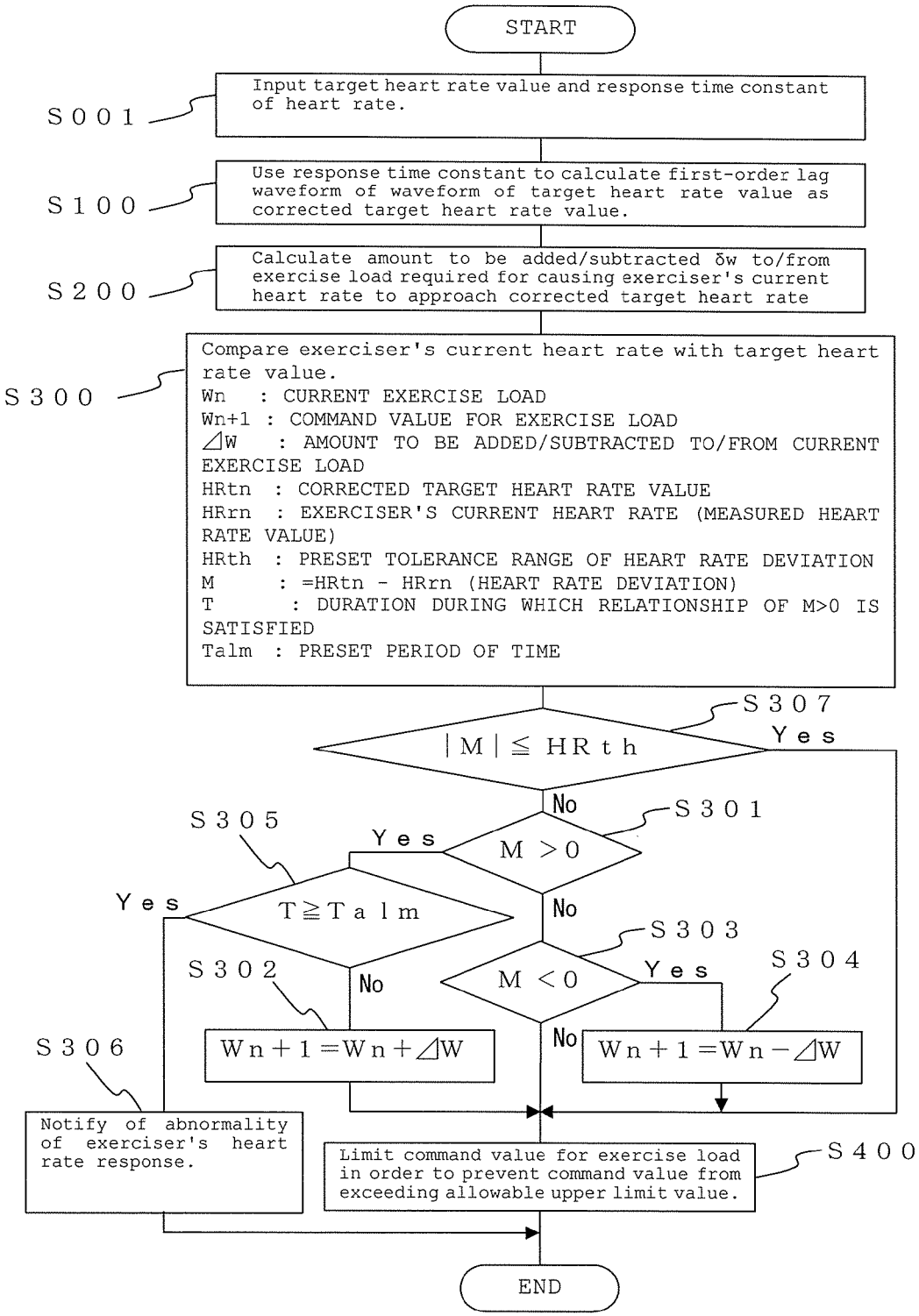
FIG. 12 is a flow chart illustrating a method of controlling an exercise therapy device according to a fourth embodiment of the present invention.

FIG. 12 is a flow chart illustrating a method of controlling an exercise therapy device according to the fourth embodiment of the present invention. In the flow chart of the fourth embodiment illustrated in FIG. 12, as compared with the flow chart of the first embodiment illustrated in FIG. 5, the processing of Steps S305 and S306 is added. Further, T and Talm are added to Step S300. Other steps are the same as those of the first embodiment described above.

In the flow chart illustrated in FIG. 12, in Step S305, the arithmetic control part 6 measures a duration T during which the absolute value M of the heart rate deviation exceeds the tolerance range of the heart rate deviation preset in the storage part 7 and the relationship of M>0 is satisfied. Then, when the duration T exceeds a period of time Talm preset in the storage part 7 in Step S300, in Step S306, the arithmetic control part 6 notifies of the abnormality of the exerciser's heart rate response on the touch panel 8 or with an alarm sound, for example.

As described above, in the fourth embodiment, when the state in which the exerciser's measured heart rate value does not rise despite the application of the command value for the exercise load continues for a period of time longer than the preset period of time, it is determined that the exerciser's heart rate response is abnormal and the abnormality notification is given. As a result, it is possible to detect an abnormal state in which the exerciser's heart rate response differs from what is expected and to prevent an excessive load from being applied to the exerciser.

In the foregoing description, it will be readily appreciated by those skilled in the art that modifications may be made to the invention without departing from the concepts disclosed herein. Such modifications are to be considered as included in the following claims, unless these claims by their language expressly state otherwise.

What is claimed is:

1. An exercise therapy device, the exercise therapy device comprising:
    a sensor for measuring a value of one of a heart rate and a pulse rate of the exerciser;
    a load control unit configured for controlling an exercise load to be applied to the exerciser;
    a load motor to be controlled by the load control unit to generate the exercise load; and
    a control apparatus comprising:
        a storage part;
        an input device for receiving an input operation from an exerciser; and
        a control part for controlling an exercise load to be applied by the load motor to an exerciser so that the measured value of one of a heart rate and a pulse rate of the exerciser, which are each an exercise physiological response of the exerciser, approaches a preset target value of the exercise physiological response, the control part being configured to:
            set the preset target value of the exercise physiological response and a response time constant of the exercise physiological response of the exerciser in the storage part of the exercise therapy device in response to an input operation of the exerciser received from the input device;
            use the response time constant to calculate a first-order lag waveform of a waveform of the preset target value of the exercise physiological response as a corrected target value of the exercise physiological response;
            calculate a difference between the preset target value of the exercise physiological response and the measured value of the exercise physiological response as an exercise physiological response deviation before correction;
            calculate a difference between the corrected target value of the exercise physiological response and the measured value of the exercise physiological response as an exercise physiological response deviation after correction; and
            generate, based on the exercise physiological response deviation before correction and the exercise physiological response deviation after correction, a command value for the exercise load so that the exercise physiological response of the exerciser approaches one of the preset target value of the exercise physiological response and the corrected target value of the exercise physiological response, to thereby control the load motor and thus control the exercise load to be applied to the exerciser.

2. The exercise therapy device according to claim 1, wherein the control part is further configured to:
    calculate, based on the exercise physiological response deviation after correction, an amount to be added/subtracted to/from the exercise load to be applied to the exerciser required for causing the exercise physiological response of the exerciser to approach the preset target value of the exercise physiological response; and
    set a current exercise load as the command value for the exercise load as it is when an absolute value of the exercise physiological response deviation after correction falls within a preset tolerance range, and calculate, when the absolute value of the exercise physiological response deviation after correction is outside the preset tolerance range, a value obtained by adding/subtracting the amount to be added/subtracted to/from the exercise load to/from the current exercise load as the command value for the exercise load.

3. The exercise therapy device according to claim 1, wherein the control part is further configured to:
calculate, based on the exercise physiological response deviation before correction, an amount to be added/subtracted to/from the exercise load to be applied to the exerciser required for causing the exercise physiological response of the exerciser to approach the preset target value of the exercise physiological response; and
set a current exercise load as the command value for the exercise load as it is when an absolute value of the exercise physiological response deviation after correction falls within a preset tolerance range, and calculate, when the absolute value of the exercise physiological response deviation after correction is outside the preset tolerance range, a value obtained by adding/subtracting the amount to be added/subtracted to/from the exercise load to/from the current exercise load as the command value for the exercise load.

4. The exercise therapy device according to claim 1, wherein the control part is further configured to:
set a heart rate rise time and a heart rate fall time of the exercise physiological response in the storage part in response to the input operation of the exerciser; and
modify the waveform of the preset target value of the exercise physiological response that changes in a stepwise manner to a waveform that changes at a constant rate of change during one of the heart rate rise time and the heart rate fall time, and then use the response time constant to calculate the first-order lag waveform of the modified waveform of the preset target value of the exercise physiological response as the corrected target value of the exercise physiological response.

5. The exercise therapy device according to claim 1, wherein:
the storage part has preset therein a table defining a relationship between each of classes of severity of a heart failure and the response time constant of the exercise physiological response of the exerciser; and
the control part is further configured to:
set one of the classes of severity that has been set in response to the input operation of the exerciser in the storage part; and
acquire the response time constant associated with the one of the classes of severity with reference to the table.

6. The exercise therapy device according to claim 3, wherein the control part is further configured to notify of an abnormality when a period of time during which an absolute value of the exercise physiological response deviation after correction is outside a preset tolerance range and the measured value of the exercise physiological response is smaller than the corrected target value of the exercise physiological response exceeds a preset period of time.

7. A control method for an exercise therapy device, the exercise therapy device comprising: a sensor for measuring a value of one of a heart rate and a pulse rate of the exerciser; a load control unit configured for controlling an exercise load to be applied to the exerciser; a load motor to be controlled by the load control unit to generate the exercise load; and a control apparatus comprising a storage part, an input device for receiving an input operation from an exerciser, a control part for controlling an exercise load to be applied by the load motor to an exerciser so that the measured value of one of a heart rate and a pulse rate of the exerciser, which are each an exercise physiological response of the exerciser, approaches a preset target value of the exercise physiological response, the control method comprising:
setting, by the control part, the preset target value of the exercise physiological response and a response time constant of the exercise physiological response of the exerciser in the storage part of the exercise therapy device in response to an input operation of the exerciser;
using, by the control part, the response time constant to calculate a first-order lag waveform of a waveform of the preset target value of the exercise physiological response as a corrected target value of the exercise physiological response;
calculating, by the control part, a difference between the preset target value of the exercise physiological response and the measured value of the exercise physiological response as an exercise physiological response deviation before correction;
calculating, by the control part, a difference between the corrected target value of the exercise physiological response and the measured value of the exercise physiological response as an exercise physiological response deviation after correction; and
generating, by the control part, based on the exercise physiological response deviation before correction and the exercise physiological response deviation after correction, a command value for the exercise load so that the exercise physiological response of the exerciser approaches one of the preset target value of the exercise physiological response and the corrected target value of the exercise physiological response, to thereby control the load motor and thus control the exercise load to be applied to the exerciser.

* * * * *

UNITED STATES PATENT AND TRADEMARK OFFICE
CERTIFICATE OF CORRECTION

PATENT NO.        : 9,600,719 B2
APPLICATION NO.   : 14/473312
DATED             : March 21, 2017
INVENTOR(S)       : Hironori Suzuki Page 1 of 1

It is certified that error appears in the above-identified patent and that said Letters Patent is hereby corrected as shown below:

In the Specification

Column 10, Line 27, "to" should be --tn--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*